(12) United States Patent
Costonis

(10) Patent No.: US 10,024,771 B2
(45) Date of Patent: Jul. 17, 2018

(54) PORTABLE SELF-CLEANING AGGREGRATE MIXTURE ANALYSIS UNIT

(71) Applicant: Joel Costonis, Dexter, ME (US)

(72) Inventor: Joel Costonis, Dexter, ME (US)

( * ) Notice: Subject to any disclaimer, the term of this patent is extended or adjusted under 35 U.S.C. 154(b) by 0 days.

(21) Appl. No.: 15/532,587

(22) PCT Filed: Feb. 23, 2017

(86) PCT No.: PCT/US2017/019043
§ 371 (c)(1),
(2) Date: Jun. 2, 2017

(87) PCT Pub. No.: WO2017/147242
PCT Pub. Date: Aug. 31, 2017

(65) Prior Publication Data
US 2018/0045625 A1    Feb. 15, 2018

Related U.S. Application Data

(60) Provisional application No. 62/299,024, filed on Feb. 24, 2016.

(51) Int. Cl.
| | | |
|---|---|---|
| B03B 1/00 | (2006.01) |
| G01N 1/34 | (2006.01) |
| G01N 1/38 | (2006.01) |
| G01N 35/10 | (2006.01) |
| G01N 15/02 | (2006.01) |
| B07B 1/38 | (2006.01) |
| G01N 1/40 | (2006.01) |
| B07B 1/46 | (2006.01) |

(52) U.S. Cl.
CPC ............... G01N 1/34 (2013.01); B07B 1/38 (2013.01); G01N 1/38 (2013.01); G01N 15/0272 (2013.01); G01N 35/1097 (2013.01); B07B 1/46 (2013.01); G01N 2001/4088 (2013.01)

(58) Field of Classification Search
CPC ........ G01N 1/34; G01N 1/38; G01N 15/0272; G01N 35/1097; G01N 3001/4088; B07B 1/28; B07B 1/38; B07B 1/40; B07B 1/42; B07B 1/46; B07B 2201/04
USPC .............. 209/233, 239, 309, 311, 315, 365.1
See application file for complete search history.

(56) References Cited

U.S. PATENT DOCUMENTS

| 5,082,553 A | 1/1992 | Tanii |
| 2008/0011110 A1 | 1/2008 | Constonis |
| 2014/0353217 A1 | 12/2014 | Presby |

FOREIGN PATENT DOCUMENTS

| KR | 10-2007-0052104 A | 5/2007 |
| KR | 10-1244089 B1 | 3/2013 |

*Primary Examiner* — Joseph C Rodriguez
*Assistant Examiner* — Kalyanavenkateshware Kumar
(74) *Attorney, Agent, or Firm* — Jeffrey Joyce, Esq.; Patricia Mathers

(57) ABSTRACT

A portable, self-cleaning aggregate mixture analysis device that accepts a sample of an aggregate mixture, separates the sample into particles, analyzes the compositions of the sample, displays results to a user and washes away sample residue, so as to prepare the device for analysis of a subsequent material sample.

7 Claims, 23 Drawing Sheets

PORTABLE SELF-CLEANING AGGREGRATE MIXTURE ANALYSIS UNIT

BACKGROUND INFORMATION

Field of the Invention

The invention relates to the field of composition analysis of aggregate materials. Further, the invention relates to equipment that is used to analyze the components of an aggregate particle mixture, such as those that are used to make asphalt concrete.

Discussion of Prior Art

Roadways, parking lots, and other surfaces that are intended to be used with wheeled vehicles are often covered in a composite material such as asphalt concrete or flexible pavement. These composite materials are composed of a mixture of variously sized aggregate particles, such as sand, gravel, crushed stone and slag, which are combined with a binder such as asphalt or bitumen. There are a number of well-known composite material mixture formulations, which combine a mixture of different size aggregate particles with various amounts of binders to create the preferred composite material for a specific purpose and to meet various standards and regulations.

The particle size distribution in the mixture of aggregate particles is one of the most influential characteristics in determining how the composite material will perform as, for example, a pavement material because the particle mixture composition influences the stiffness, stability, durability, permeability, workability, skid resistance and resistance to moisture damage of the pavement. For example, a mixture that does not contain sufficient large sized particles may result in a composite material that lacks stability. Alternatively, a mixture that contains too high a percentage of large particles may result in a composite material that has poor workability.

While various aggregate mixture formulations are known, the different formulations are not available as premixed compositions; rather, the various aggregates must be purchased separately and mixed together to obtain the composition that corresponds to a project specification.

The blending process generally involves combining and mixing an estimated amount of variously sized particles in a mixer, using a scale to weigh the mixture, transporting the mixture to a drying machine to dry the mixture, using a scale to weigh the dry mixture, using a sorting mechanism to sort the aggregate particles by particle size and then using the scale to weigh each size group. Then analyzing weights to determine whether the mixture has the desired composition. These test steps typically result in a cumbersome process that involves numerous machines and that allow for a great deal of human error. And, typically, these tests may only be done in a lab rather than at a mixing site, thus introducing additional delay, cost, and opportunity for human error.

What is needed, therefore, is a conveniently sized portable test unit that is capable of sorting and analyzing the mixture of aggregates at a worksite. What is further needed is such a test unit that is in a ready-to-use condition after a test has been completed.

BRIEF SUMMARY OF THE INVENTION

The invention is a portable self-cleaning aggregate material analysis device that accepts a sample of an aggregate particle mixture, captures the weight of the initial sample, dries the sample, and separates and sorts the sample by particle size, and then captures the weight of those particle size groupings to determine the composition of the sample aggregate mixture, then displays the information to a user, and washes away residual sample material, so that the device is ready to use for a new test.

The device includes a material analysis chamber that accepts the sample of an aggregate mixture and includes a sorting unit and a weighing mechanism. The weighing mechanism captures the wet weight of the aggregate mixture sample and relays the information to a user via an integrated computer system. A moisture evacuation system is connected to the outside of the material analysis chamber and dries the sample material by evacuating the moisture from the chamber after the wet weight is recorded. The weighing mechanism measures the dry weight of the aggregate mixture sample and relays that data to the computer system. The sorting unit then separates the dry aggregate mixture sample into individual particles and sorts those particles by particle size. The weighing mechanism then captures the weight of each group of particles.

The sorting unit includes a sieve container that holds a plurality of sieves, the sieve container having an approximately cylindrical sidewall, an open top, and a closed bottom. The sieves are fixed in the horizontal plane within the material analysis chamber, but movable in the vertical plane. The sieves have apertures that are approximately uniformly sized within a single sieve, but that vary between sieves, and are stacked inside the sieve container with the sieve at the top of the stack having the largest apertures and each successively lower sieve having slightly smaller apertures. As the sample material is separated into particles, the particles fall through the sieves having apertures that are larger than the particle size until the particles land in, and are contained by, a sieve having apertures smaller than the particle.

The sorting unit also includes a vertical oscillation mechanism to facilitate the particles falling through the sieves. This vertical oscillation mechanism includes an oscillator ring having an upper edge that is a vertical displacement contour. The ring is rotatably affixed in the base of the material analysis chamber and is connected to a motor located outside of the material analysis chamber. Actuating the motor causes the oscillator ring to rotate. A plurality of wheels are affixed to the bottom of the sieve container's sidewall and sit on top of the oscillator ring. As the ring rotates beneath the wheels, the displacement contour on the ring forces the sieve container to oscillate in the vertical plane, thereby causing the aggregate particles fall through the sieves that have sieve apertures that are larger than their particle size.

Following the test, the computer system relays the moisture content of the aggregate mixture and the ratio of particles sizes contained within the sample, the particles are manually removed from the device and a washing system cleans the chamber of all sample material residue to prepare the chamber for further sample material analysis. The device is relatively small and light, such that it is portable and may be transported in the back of an average size pickup truck and easily moved by two or more individuals having average physical capabilities.

BRIEF DESCRIPTION OF THE DRAWINGS

The present invention is described with reference to the accompanying drawings. In the drawings, like reference numbers indicate identical or functionally similar elements. The drawings are not drawn to scale.

DETAILED DESCRIPTION OF THE INVENTION

Figure 1:
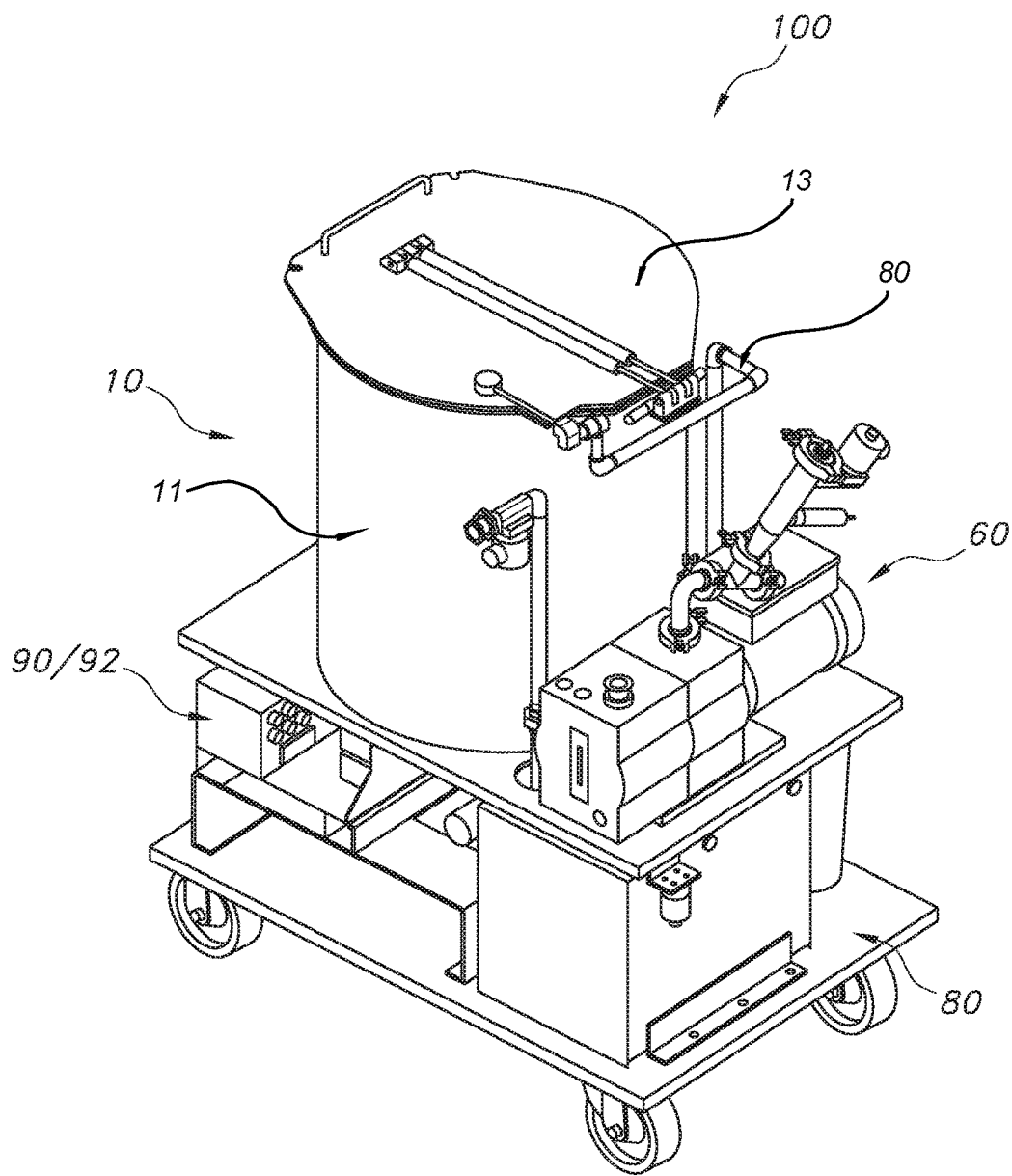
FIG. 1 is a perspective view of the device according to the invention.
Figure 2:
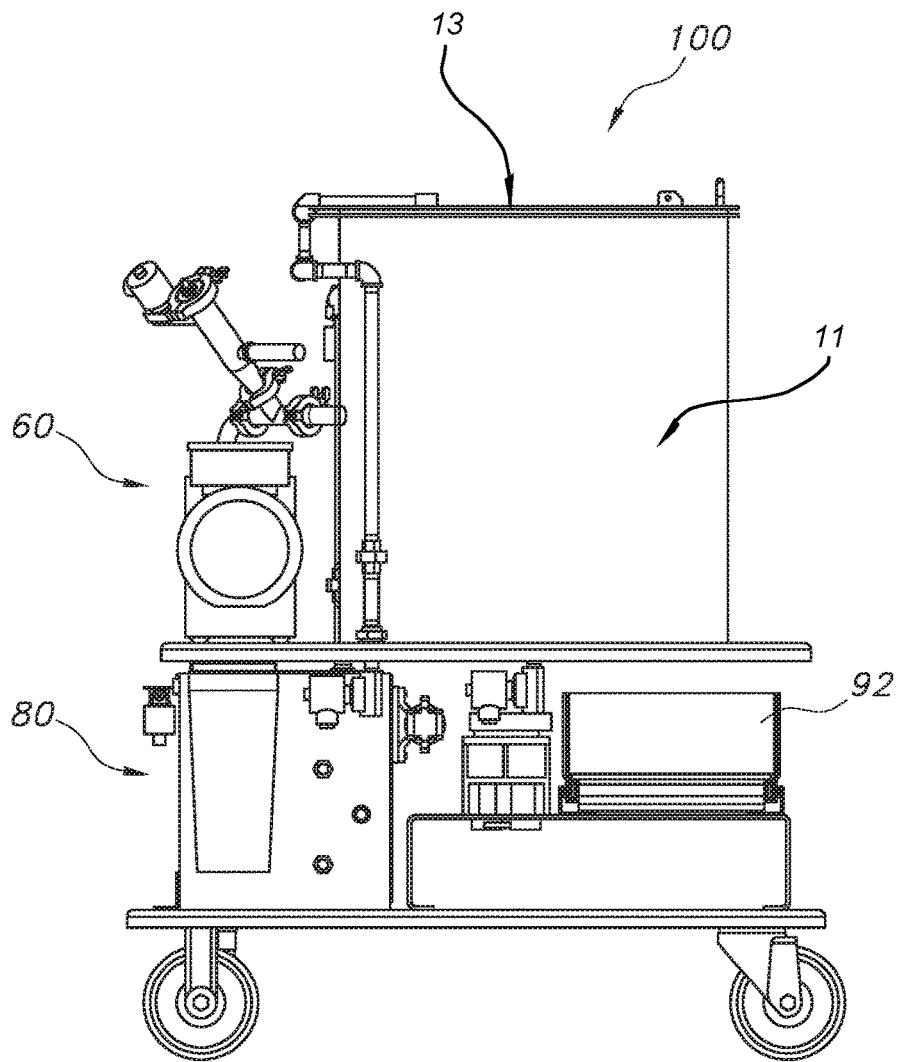
FIG. 2 is a side view of the device.
Figure 3:
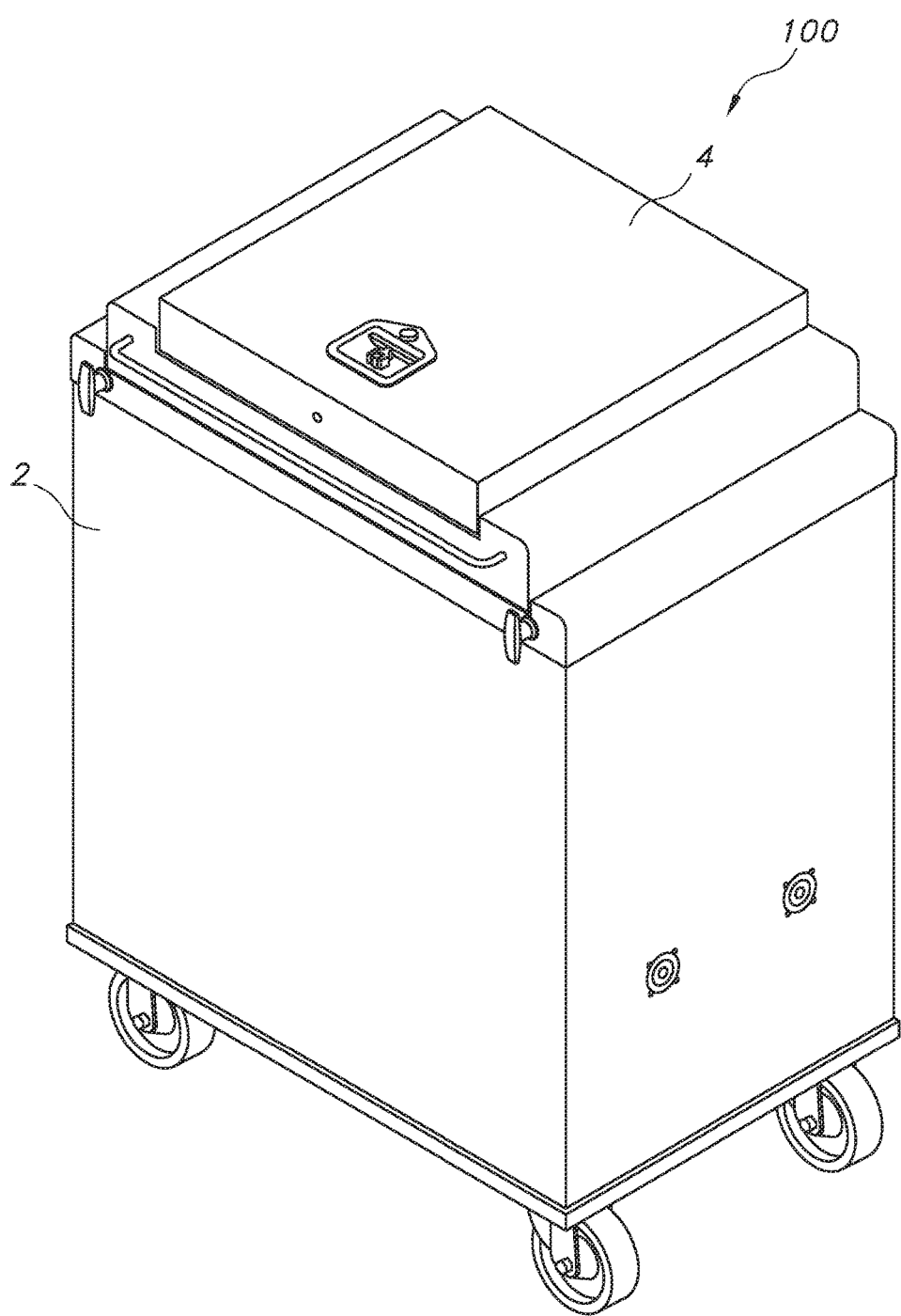
FIG. 3 is a perspective view of the device encased in a chassis.
Figure 4:
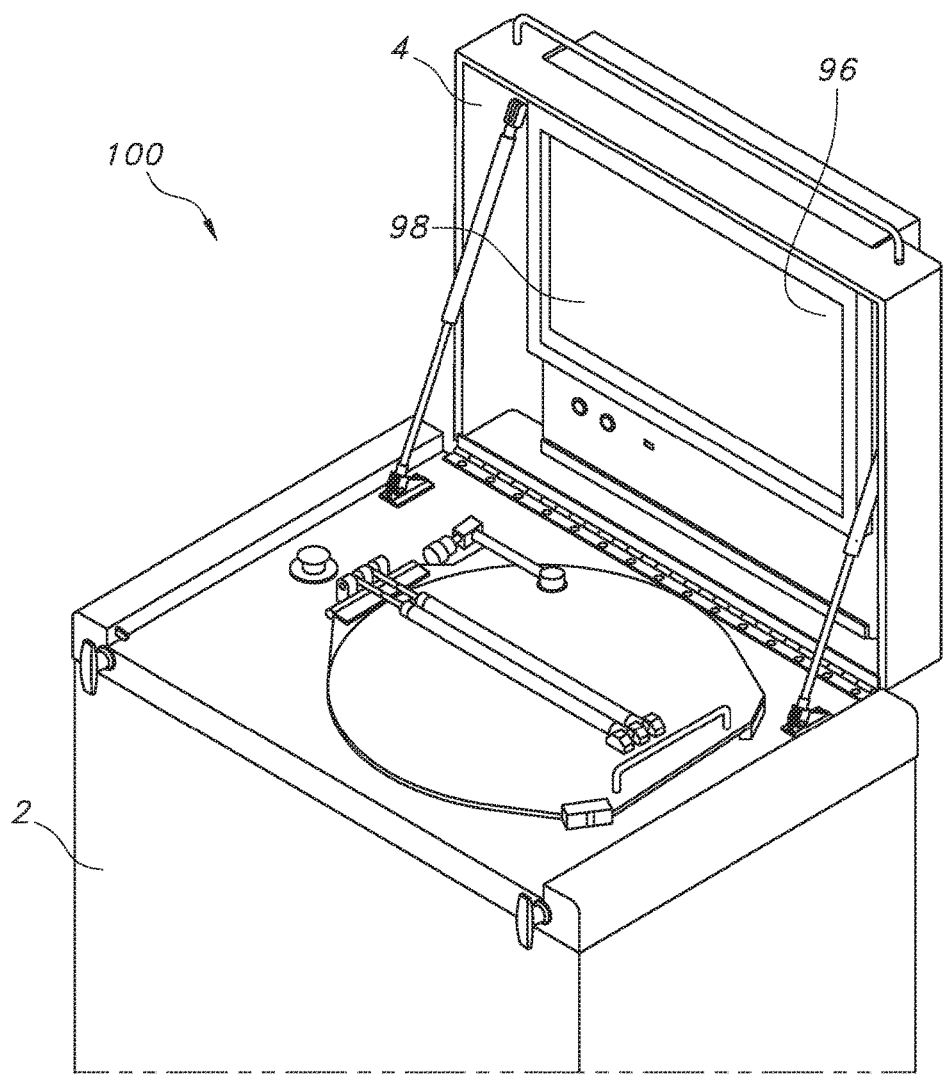
FIG. 4 is a perspective view of the chassis with an open lid.

The present invention will now be described more fully in detail with reference to the accompanying drawings, in which the preferred embodiments of the invention are shown. This invention should not, however, be construed as limited to the embodiments set forth herein; rather, they are provided so that this disclosure will be complete and will fully convey the scope of the invention to those skilled in the art.

FIGS. 1-4 illustrate the portable self-cleaning aggregate mixture analysis unit 100 according to the invention, including a material analysis chamber 10 for holding a sorting unit 30 and weighing unit 49, each shown in FIGS. 5-11, a moisture evacuating unit 60, a washing unit 80, and a computer control system 90, which analyzes the contents of aggregate materials, such as used to create asphalt concrete. The material analysis chamber 10 is approximately cylindrical in shape having a sidewall 11 and a lid 13. In the embodiment shown, all of these components are contained within a chassis 2 that has a chassis lid 4 and is mounted on a movable base that is fitted with wheels or castors, and that is sized so as to be easily portable, for example, in the back of a standard size pickup truck.

To use the aggregate mixture analysis device 100 a user places an aggregate mixture sample (not shown) into the sorting unit 30 and closes the lid 13. Closing the lid creates an air tight seal of the material analysis chamber. Most samples contain a small amount of moisture, and the weighing unit 49 is first used to measure the wet weight of the sample. The moisture evacuating unit 60 then uses a vacuum pump 64 to vent the moisture out from the material analysis chamber 10 to dry the sample. The dry weight of the sample is measured and the computer control system 90 calculates the percentage of moisture in the sample, based on the difference of wet to dry weight. The sorting unit 30 then sorts the aggregate mixture by particle size, and the weighing unit 49 weighs each size group. Once the test is completed, a user manually empties the sorting unit 30 and actuates the washing unit 80 to wash away any leftover sample particles and particle residue from the sorting unit 30.

FIGS. 5-10 illustrate a first embodiment of the material analysis chamber 10 and the sorting unit 30. In this embodiment, the material analysis chamber 10 has a plurality of guide tracks 12, shown in FIGS. 5 and 6. The sorting unit 30 includes a sieve container 31, illustrated in FIGS. 5, and 7-10. The container 31 is similar in shape to that of the material analysis chamber 10, but smaller, and with a plurality of guide posts 46. This sieve container 31 has a sidewall 32, a bottom 34, and an open top 36 and fits into the material analysis chamber 10, with the guide posts 46 fitting into the guide tracks 12 on the chamber, so as to fix the position of the sieve container 31 in the horizontal plane inside the material analysis chamber.

Figure 12:
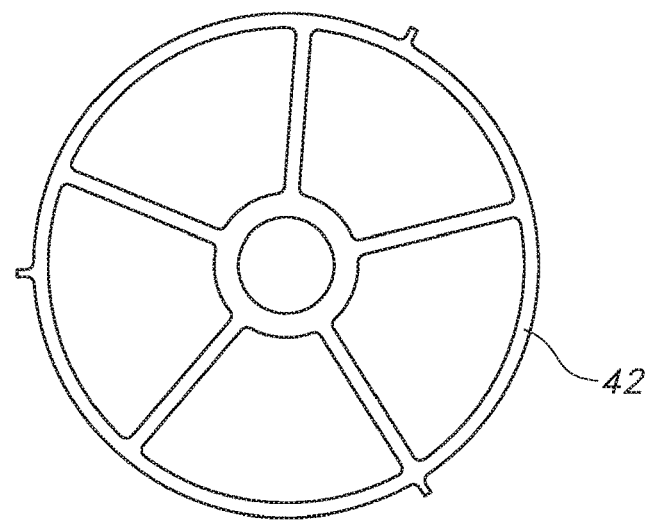
FIG. 12 is a top plan view of a sieve support ring.
Figure 13:
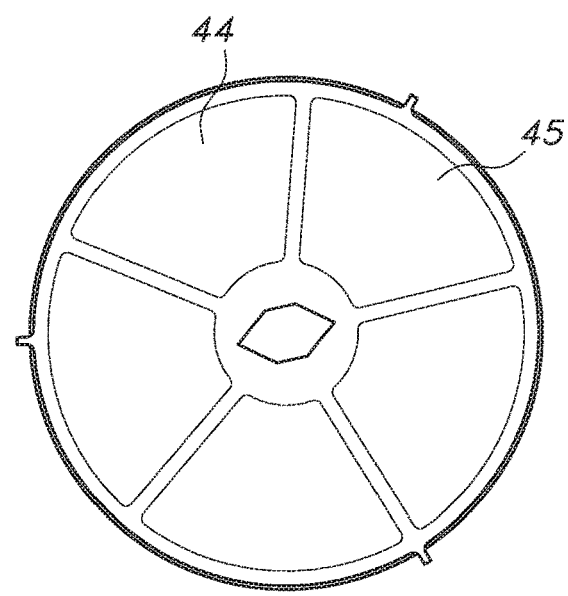
FIG. 13 is a top plan view of the sieve.

The sieve container 31 contains a graduated sieve unit that includes a plurality of screens or sieves 44, shown in FIG. 13, and a corresponding plurality of sieve support rings 42, shown in FIG. 12. Each sieve 44 comprises a sidewall made of a rigid material and a sieve plate 43 constructed of a suitable mesh material that has a plurality of sieve apertures 45. The sieves 44 are approximately circular in shape and are sized to sit loosely sit on top of the sieve support rings 42. A series of stepped ring mounts 38 are provided along the inner surface of the container sidewall 32 for supporting the plurality of sieve support rings 42. The sieve apertures 45 are uniform within a single sieve 44 but vary in size between the sieves 44, with the sieve 44 at the top of the sieve container 31 having the largest apertures 45 and each successively lower sieve 44 having slightly smaller apertures 45. The size of the apertures may vary depending on the intended application; however, for example, apertures ranging in size from 19 millimeters to 7.5 microns are often reasonable. The sieves 44 may also sit directly on the stepped ring mounts 38, however, it is common for some sieve plates 43 to be made of thin materials and in these instances the sieve support rings 42 provide support for the sieve plates 43.

Figure 14:
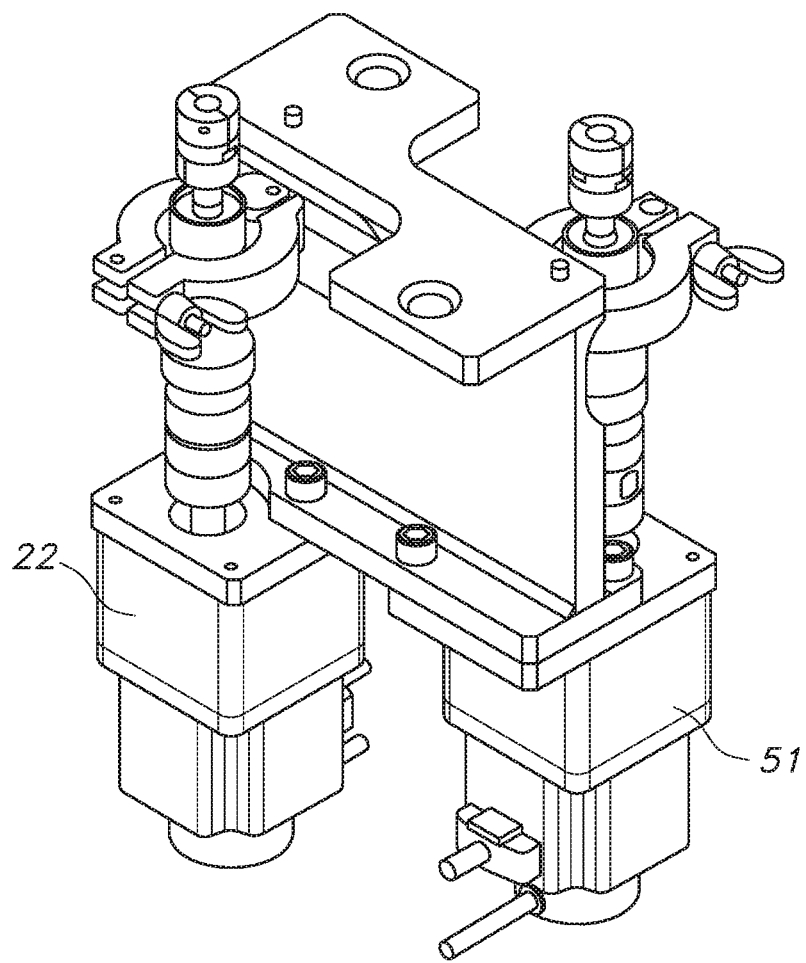
FIG. 14 is a perspective view of the stepper motors that drive the elevator post and oscillating ring.
Figure 15:
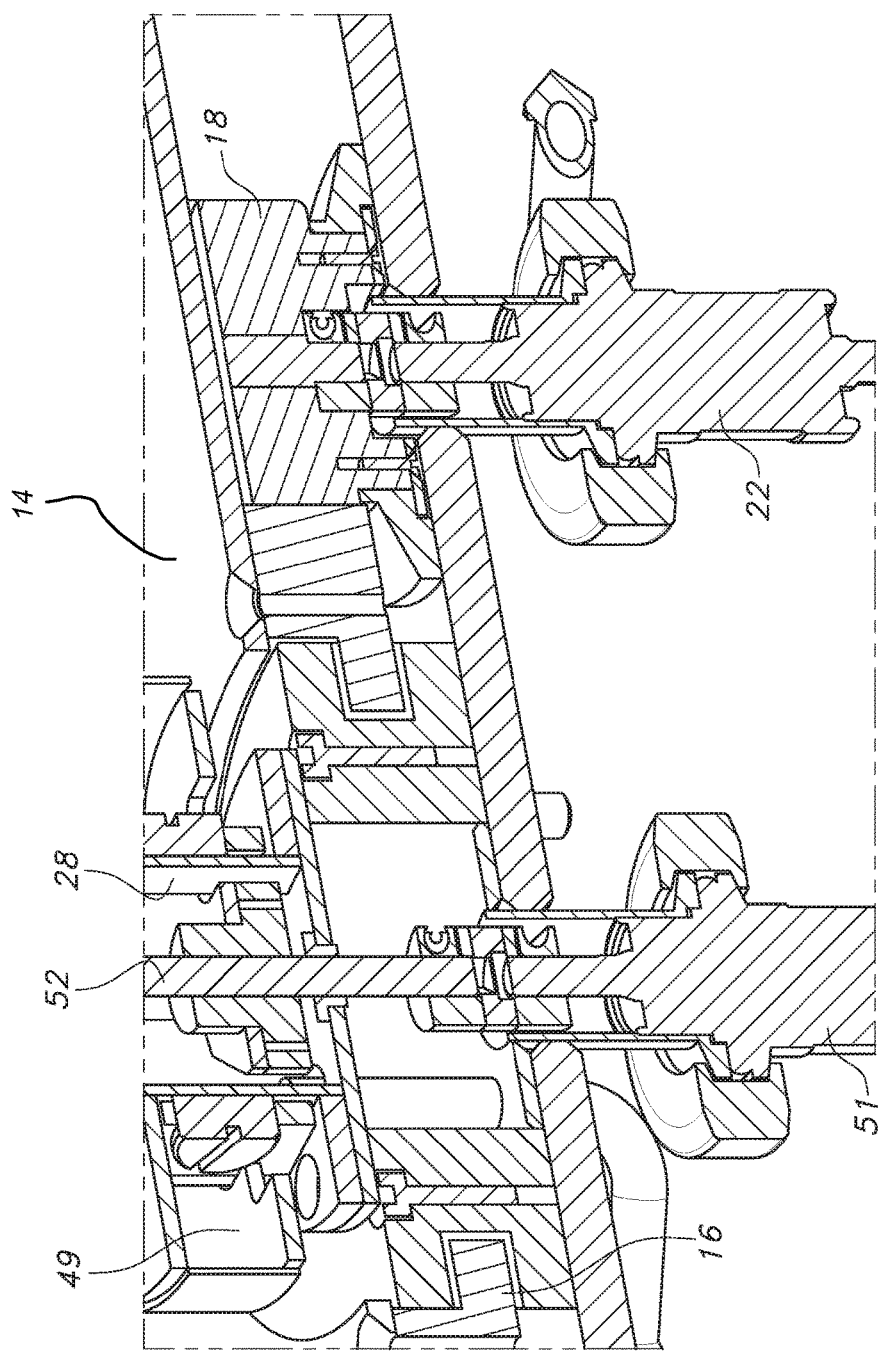
FIG. 15 is a partial cut-away view showing the motors connected to the gear and threaded rod.
Figure 16:
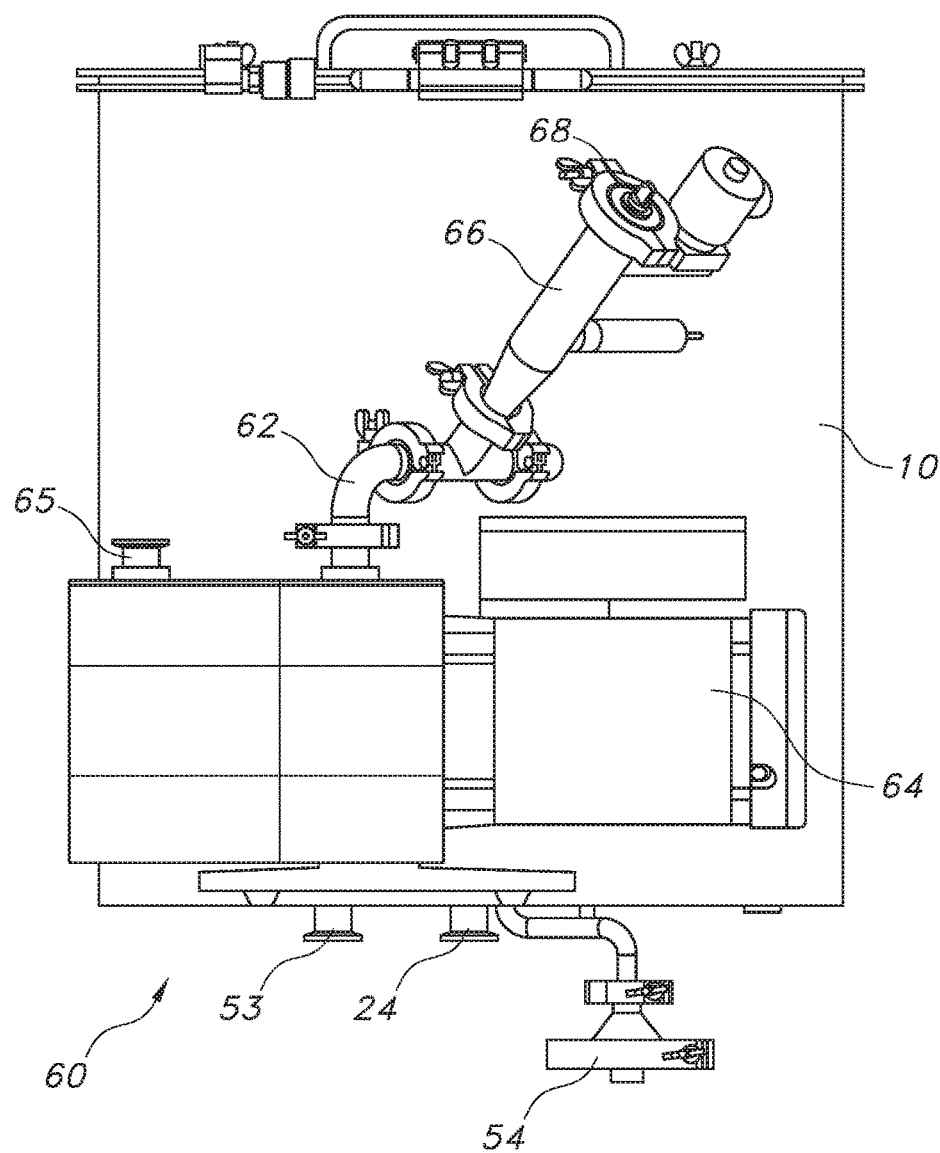
FIG. 16 is a front view of the moisture evacuating unit.
Figure 17:
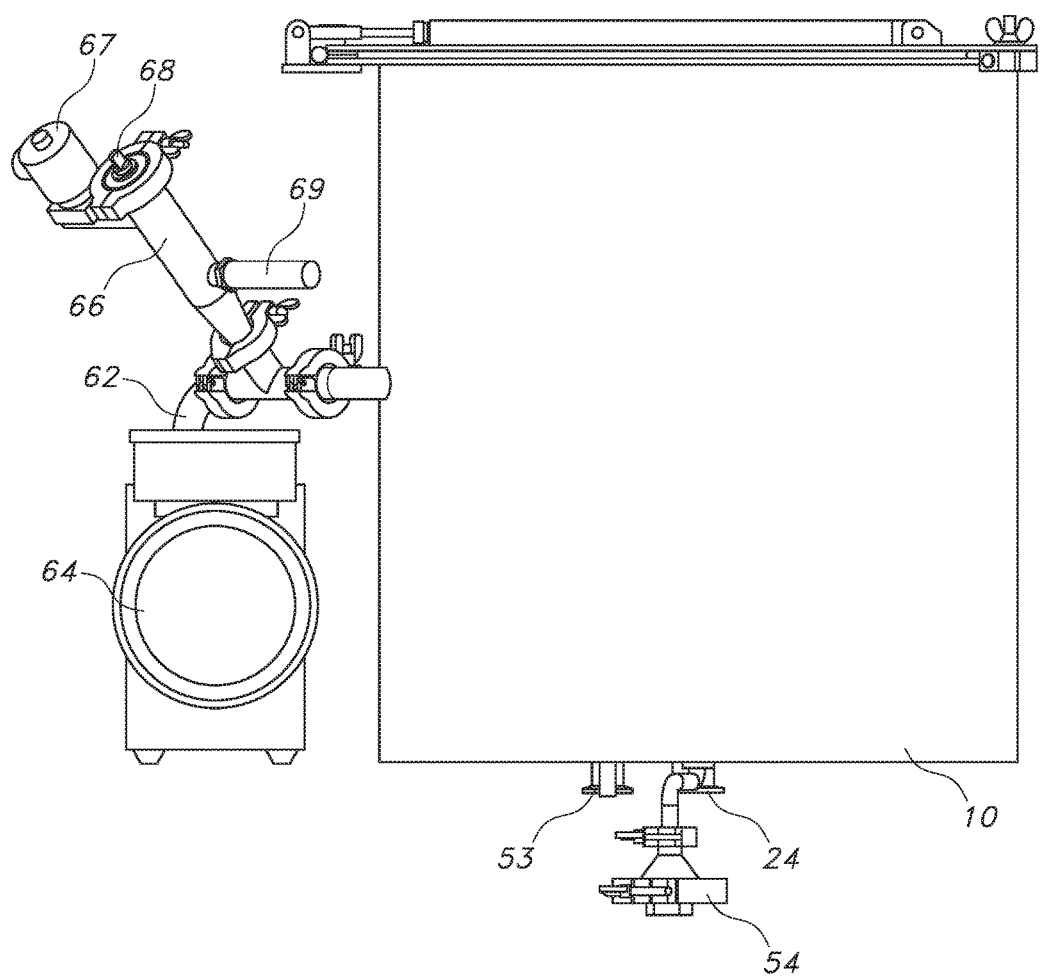
FIG. 17 is a side view of the moisture evacuating unit.
Figure 18:
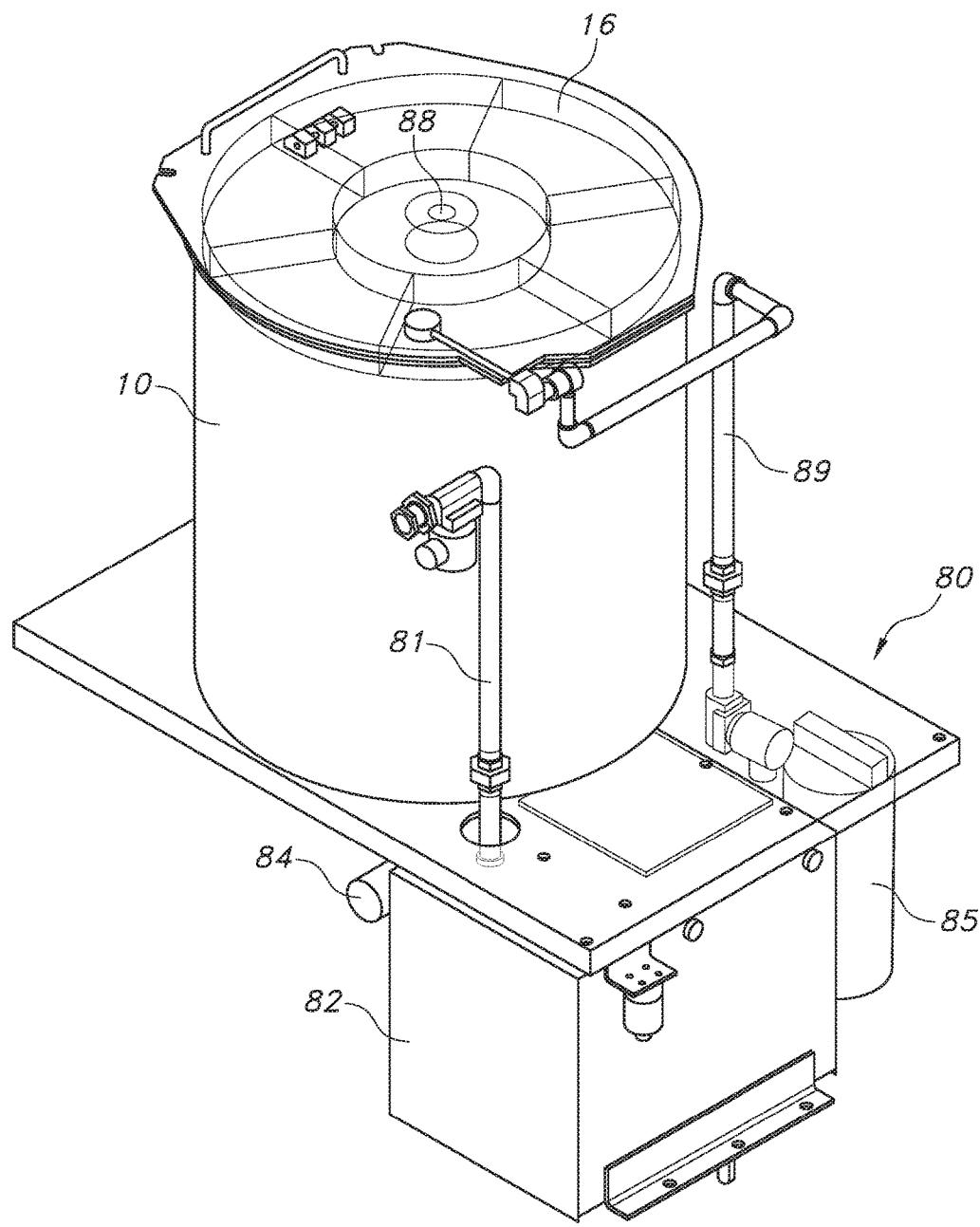
FIG. 18 is a perspective view of the washing unit.
Figure 19:
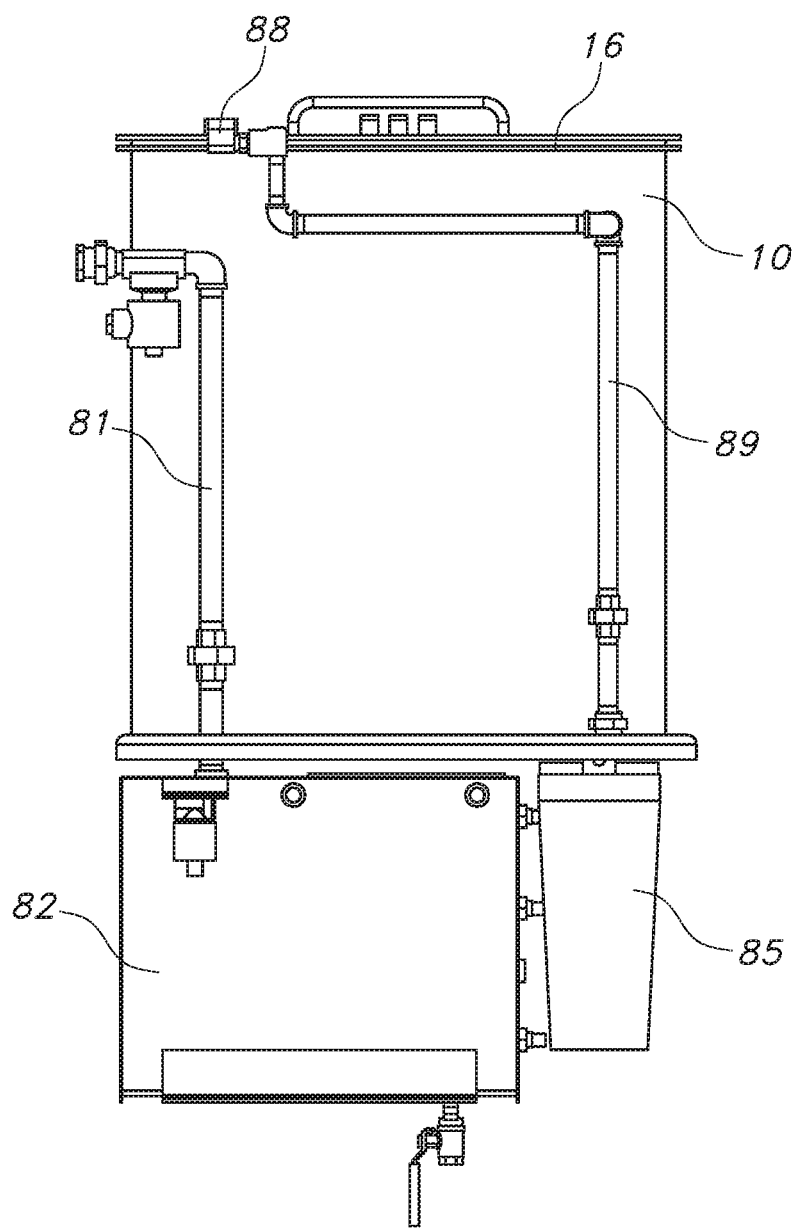
FIG. 19 is a front view of the washing unit.
Figure 20:
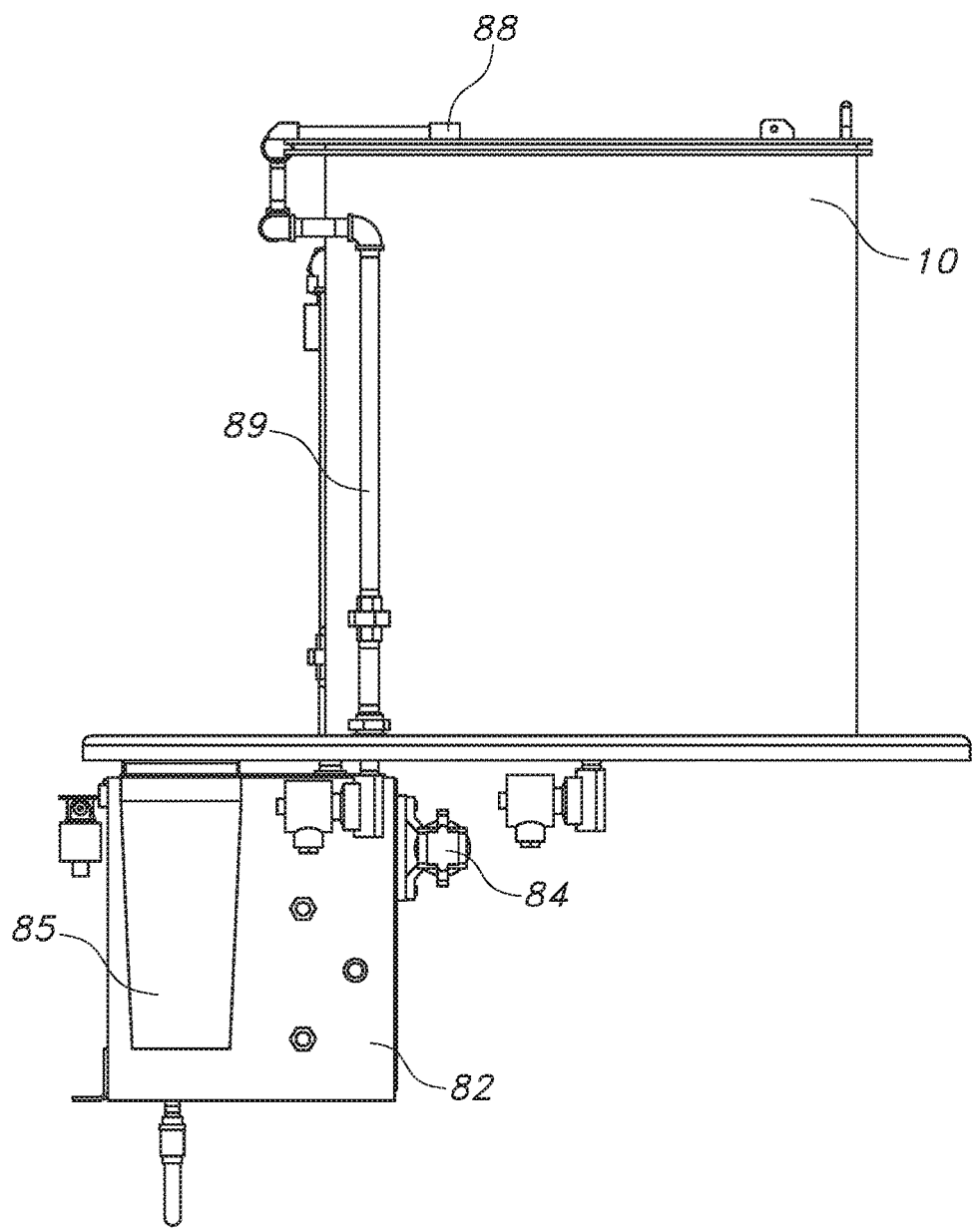
FIG. 20 is a side view of the washing unit.
Figure 21:
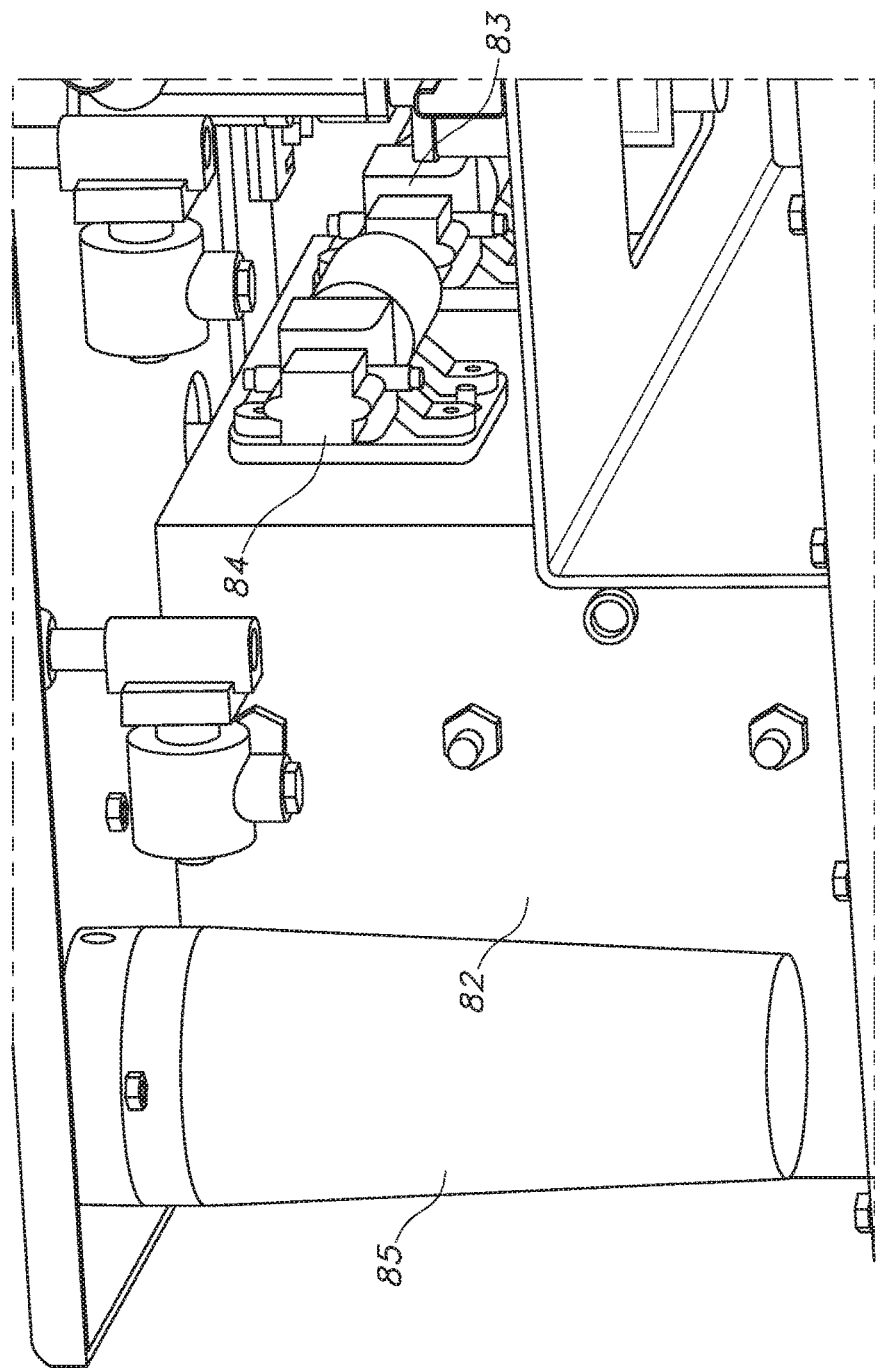
FIG. 21 is a perspective view of a portion of the washing unit showing the water pumps.

The sorting unit 30 has a vertical oscillator 33 that is used to separate the aggregate particles and sort the particles into the plurality of sieves 44. The vertical oscillator 33 includes an oscillation ring 14, shown in FIGS. 7 and 8, that is positioned in the bottom of the material analysis chamber 10 and fixedly connected to a first gear 16, shown in FIGS. 6 and 11. The first gear 16 meshes with a second gear 18 that is attached to a first stepper motor 22, which is shown in FIGS. 14 and 15, located on the outside of the material analysis chamber 10. A gear access port 24, shown in FIGS. 16 and 17, provides an opening for the motor 22 to connect to the second gear 18. The oscillation ring 14 is generally cylindrical in shape and has a top edge that is a vertical displacement contour 26.

This vertical oscillation motion is driven by the first stepper motor 22, the first and second gears, 16 and 18, and the oscillator ring 14. Actuating the first stepper motor 22 forces the second gear 18 and the first gear 16 to rotate, which in turn forces the ring 14 to rotate. As the ring 14 rotates, the wheels 48, which are mounted at fixed positions on the sieve container wall 32 and seated on the vertical displacement contour 26, are forced up and down, resulting in a vertical oscillation of the sieve container 31, along with the plurality of sieves 44. This vertical oscillation agitates the aggregate mixture sample, causing the particles to separate and then, depending on particle size, drop through the successively mounted sieves 44, so that sample particles that are smaller than the respective sieve aperture 45 fall from one sieve 44 into a lower sieve 44 until they are captured on a sieve having an aperture size smaller than the particular particle size. Any reasonable rotational speed of the ring 14 causes the sample to separate into particles, however, faster speeds cause the sample to separate faster. There are a number of suitable motors, for example, the RKII stepper motor and driver made by MICROSTEP.

Figure 5:
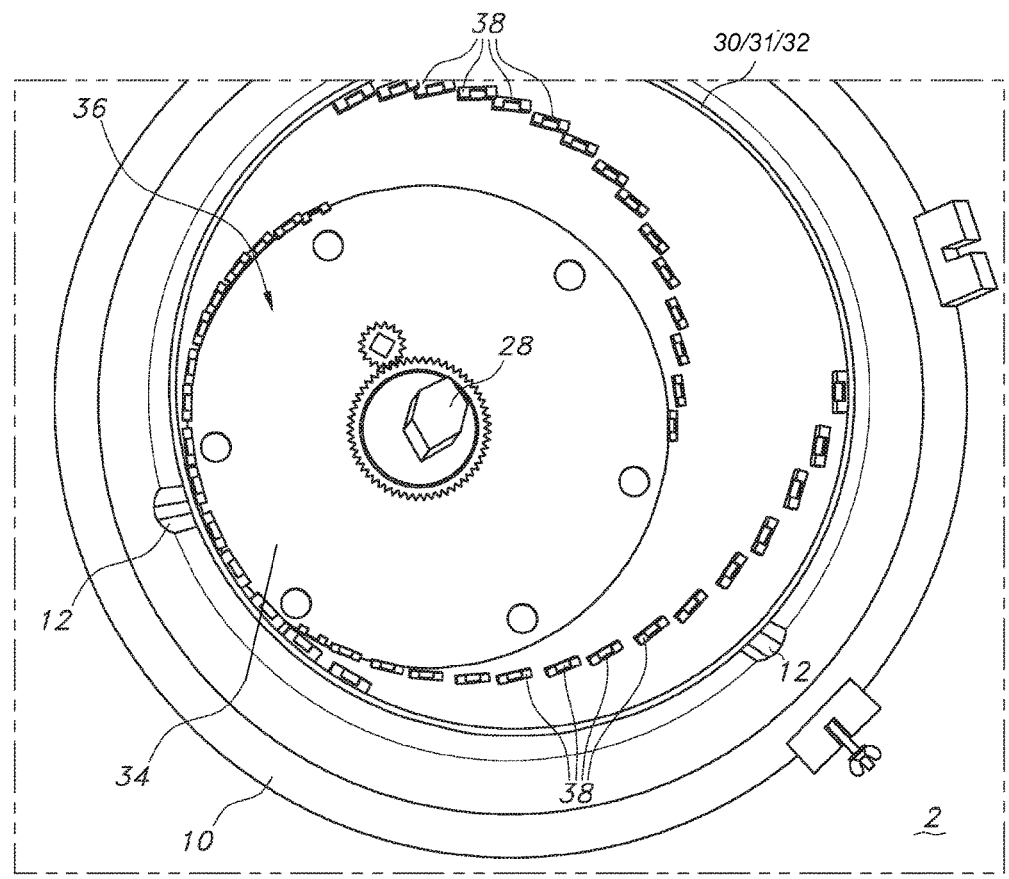
FIG. 5 is a top view of the material analysis chamber with the sieve container.
Figure 6:
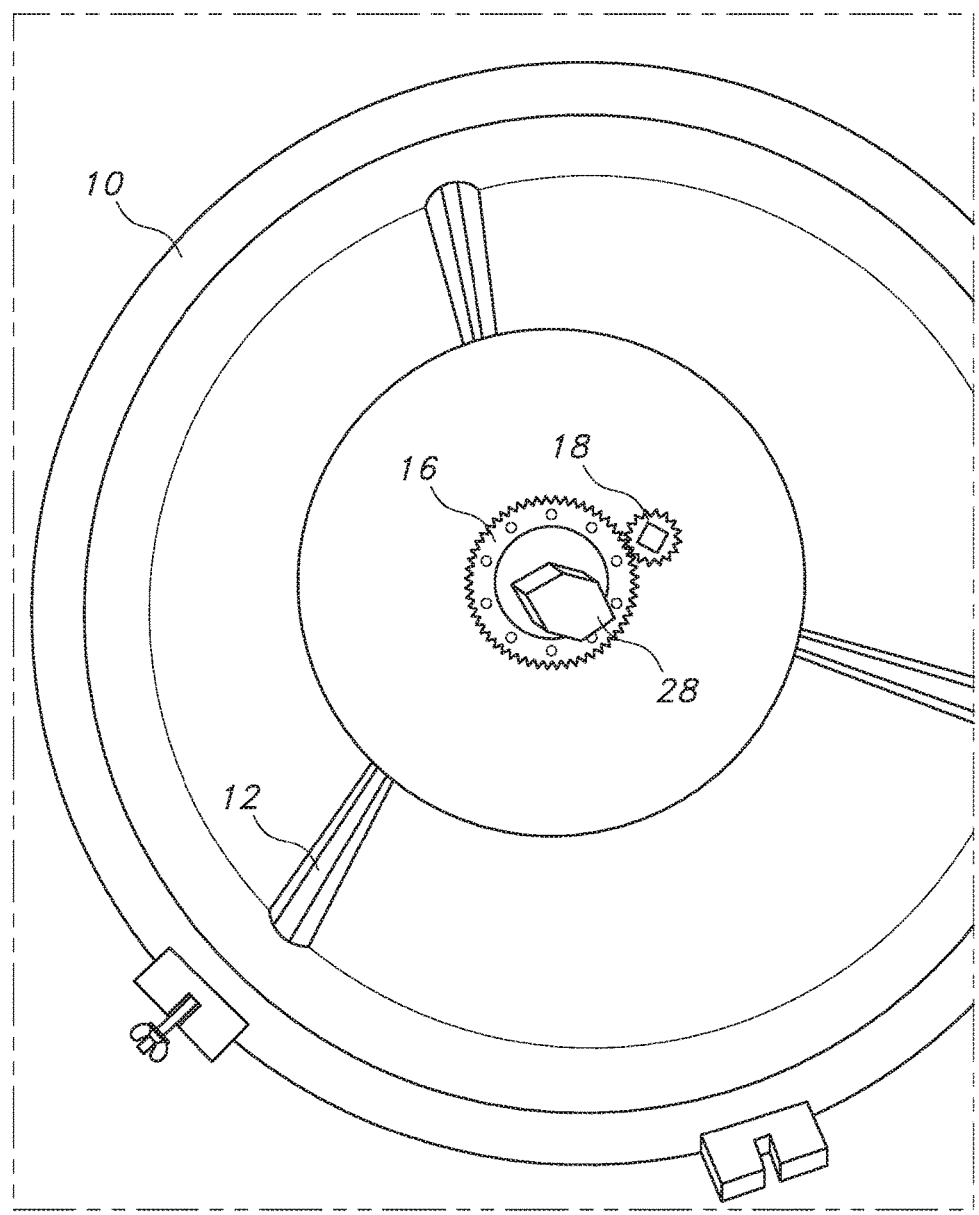
FIG. 6 is a partial top view of the material analysis chamber without the sieve container.
Figure 7:
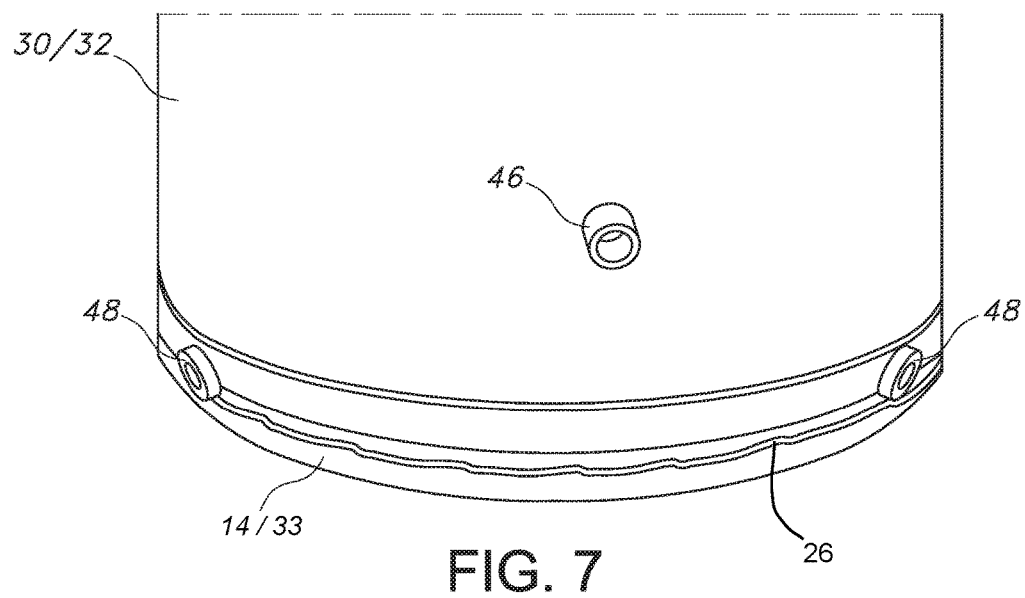
FIG. 7 is a partial side view of the sieve container showing the wheels, guide posts and the material analysis chamber's oscillating ring.
Figure 8:
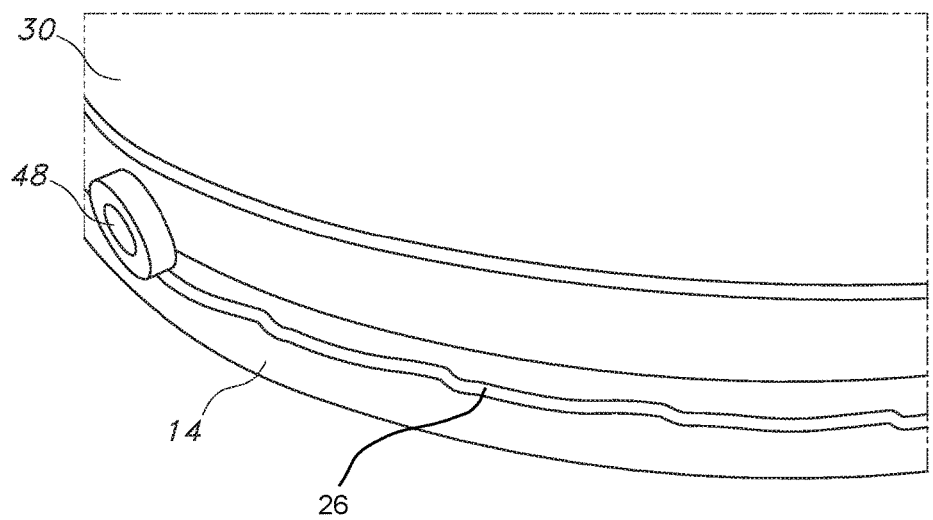
FIG. 8 is a side view of the sieve containers wheel on the material analysis chamber's oscillating ring.
Figure 9:
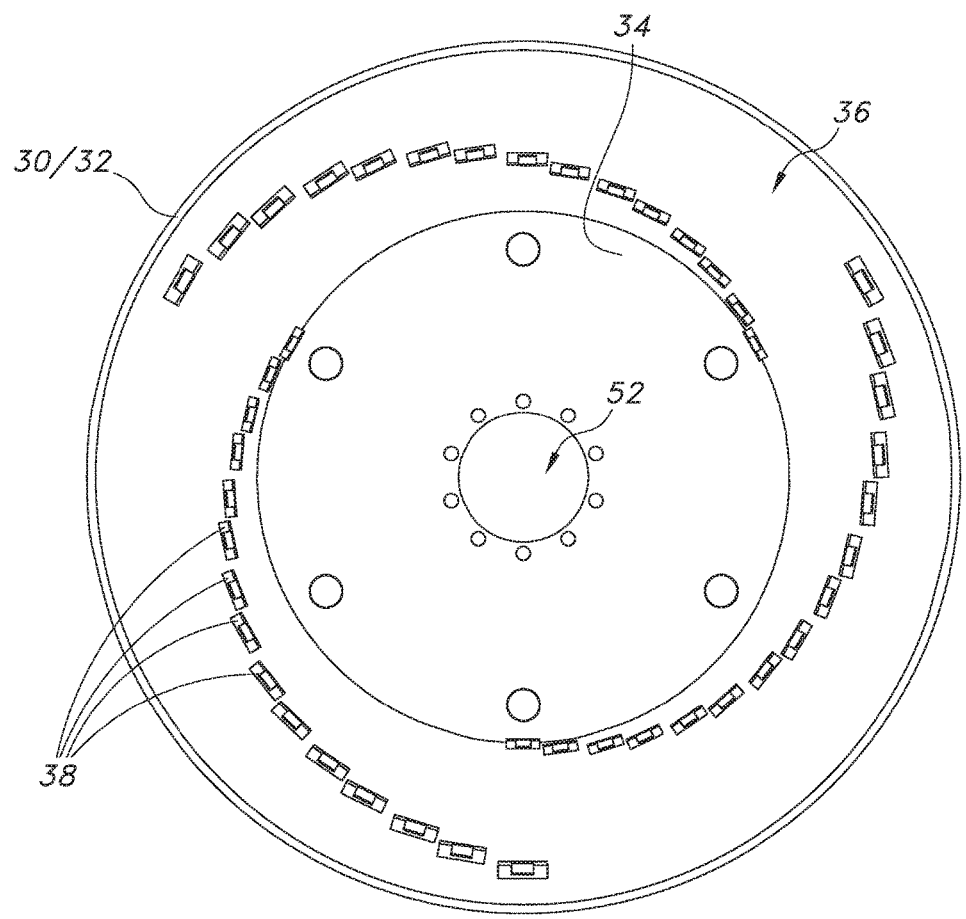
FIG. 9 is top view of the sieve container showing the inside of the unit.
Figure 10:
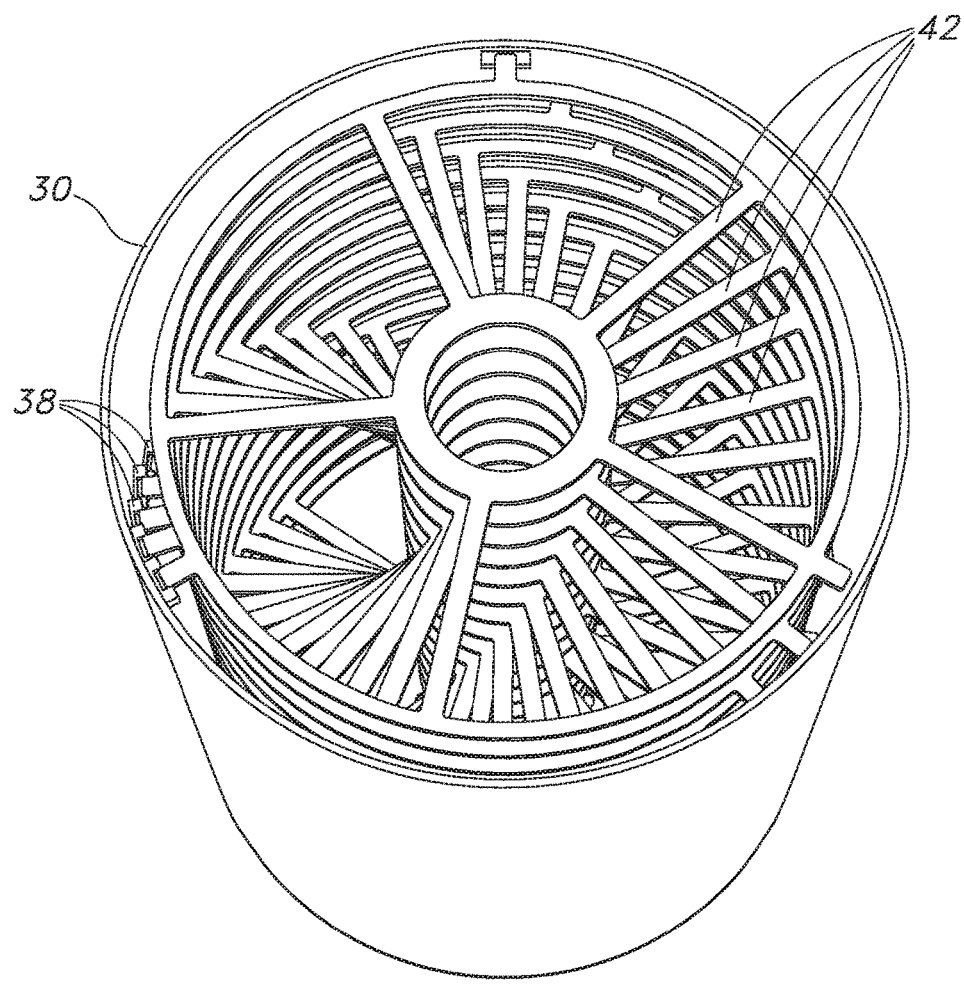
FIG. 10 is a top view of the sieve container loaded with sieve support rings.
Figure 11:
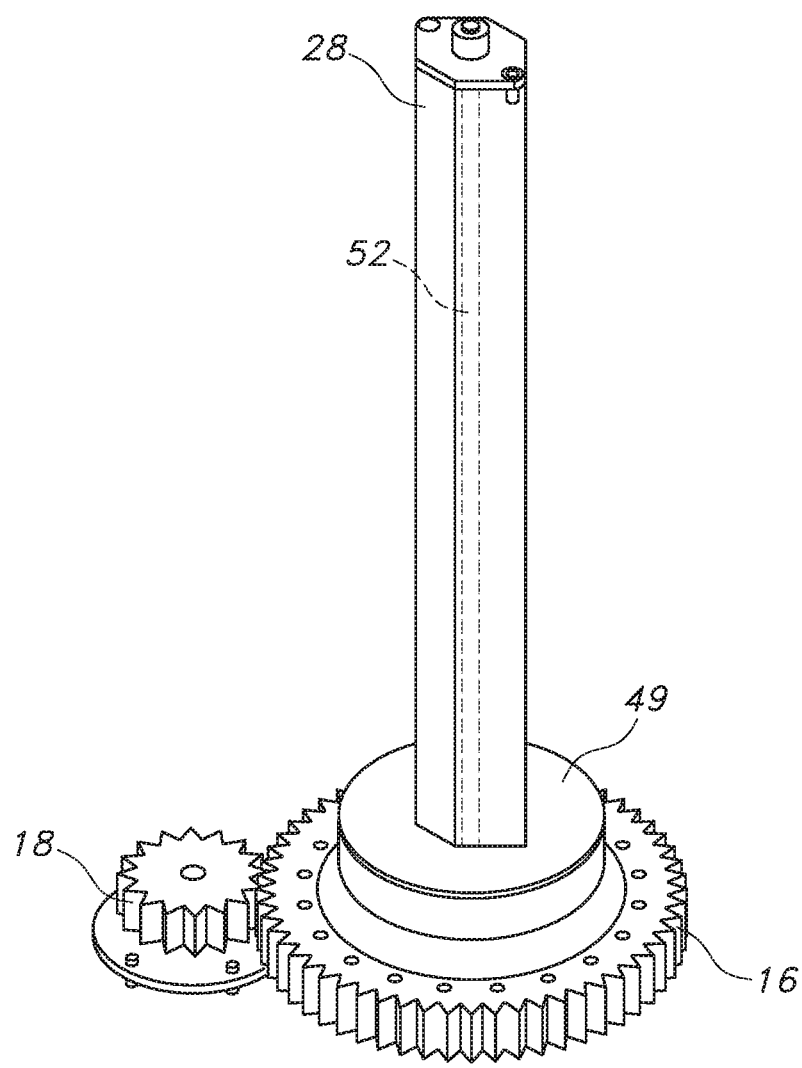
FIG. 11 is a perspective view of the elevator post and gears.

FIGS. 5, 6, and 11 show an elevator post 28 that is mounted in the center of the material analysis chamber 10 and extends upward through an opening 52 in the sieve container 31. As shown in FIG. 13, each sieve 44 has a slot 47 approximately in the middle of the sieve 44 and that is sized to fit over the elevator post 28. In the embodiment shown, the elevator post 28 has an elongate hexagonal shape and the slot 47 a shape that fits over the shaft 28, such that the sieves 44 are prevented from rotating in a horizontal plane around the elevator post 28.

FIGS. 11 and 15 illustrate a weighing mechanism 49 that is slidably coupled to the elevator post 28. A second stepper motor 51 drives a threaded rod 52 that extends congruent with a central axis that extends through the elevator post 28 and that is coupled to the weighing mechanism 49. In the embodiment shown, the weighing mechanism 49 is an elevator disc that contains one or more load cells. A rod access port 53, shown in FIGS. 16 and 17, provides an opening for the motor 51 to connect to the threaded rod 52. The second stepper motor 51 turns the rod 52 causing the weighing mechanism 49 to rise. As the weighing mechanism 49 reaches each sieve support ring 42, it lifts each support ring 42 and sieve 44, stacking the plurality of supports rings 42 and sieves 44 as it travels upward, and calculates the weight of the particle material captured on each sieve 44 by measuring the weight of the stack of sieve rings and sieve plates and subtracting the weight of the sieves 44, sieve rings 42 and previously weighed particles. The weighing mechanism 49 transmits the information back to the computer control system 90 through an instrumentation feedthrough channel 54. As the weighing mechanism 49 continues upward, it lifts each successive sieve plate 42 as it travels, transmitting the data to the computer control system 90 as it captures each sieve support ring 42.

FIGS. 16 and 17 illustrate the moisture evacuating unit 60, which is located outside of the material analysis chamber 10 and is connectable to the sidewall 12 of material analysis chamber 10 by any suitable pipe or tube 62. The moisture evacuating unit 60 includes a vacuum pump 64 with a moisture vent 65 and a moisture sensor 66. When the moisture evacuating unit 60 is activated, the pump 64 pulls the moisture from inside the material analysis chamber 10 and past the moisture sensor 66 and out through the moisture vent 65. The moisture sensor 66 indicates the current level of moisture being drawn from the material analysis chamber 10 and conveys that data to the computer system 90. Running the moisture evacuating unit 60 until the moisture sensor 66 indicates that there is no moisture in the sieve container 10 leaves a dry sample stored in the material analysis chamber 10. Also shown is a solenoid valve 67 and a pressure transducer 69 that help to monitor and control the pressure of the moisture evacuating unit 60 if needed.

In the embodiment shown, the moisture sensor includes a humidity probe (not shown) within the sensor 66 and a USB feedthrough device 68 that transmits the humidity readings to the computer control system 90.

FIGS. 18-21 illustrate the washing unit 80, which is provided to clean the chamber after it is used, and includes a water tank 82, a first water pump 83, second water pump 84, and water filter 85 and hosing 86/89 to deliver the water to the material analysis chamber 10 and sorting unit 30. The water tank 82 is filled with clean water (not shown). The first water pump 83 is connected to the water tank 84 and to the water filter 85 by any suitable tubing or hosing 86, and the water filter 87 is connected to a wide angle nozzle 88 located in the chamber lid 16 by any suitable tubing or hosing 89. Activating the first water pump 83 delivers water from the water tank 82 to the wide angle nozzle 88 which sprays water throughout the sieve container 31. The second water pump 84 connects the water tank 82 to a drain pipe 81 in the material analysis chamber 10 and pumps the water out of the material analysis chamber 10 back into the water tank 82 and subsequently, as needed, through the filter 85 to the material analysis chamber 10 for additional washing.

Figure 22:
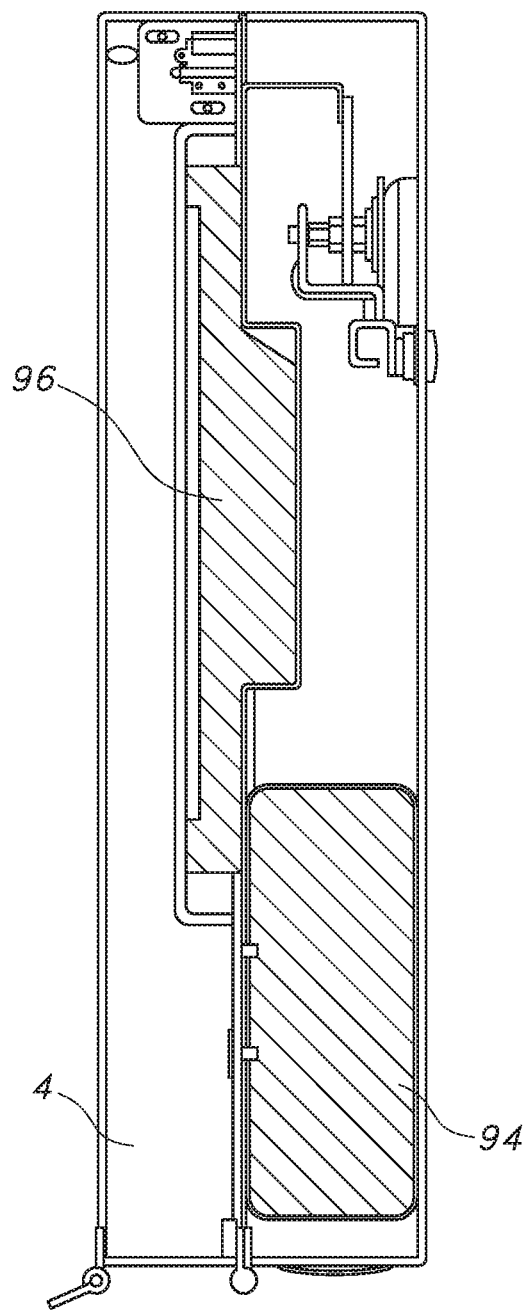
FIG. 22 is a side view of the computer system contained with the chassis lid.
Figure 23:
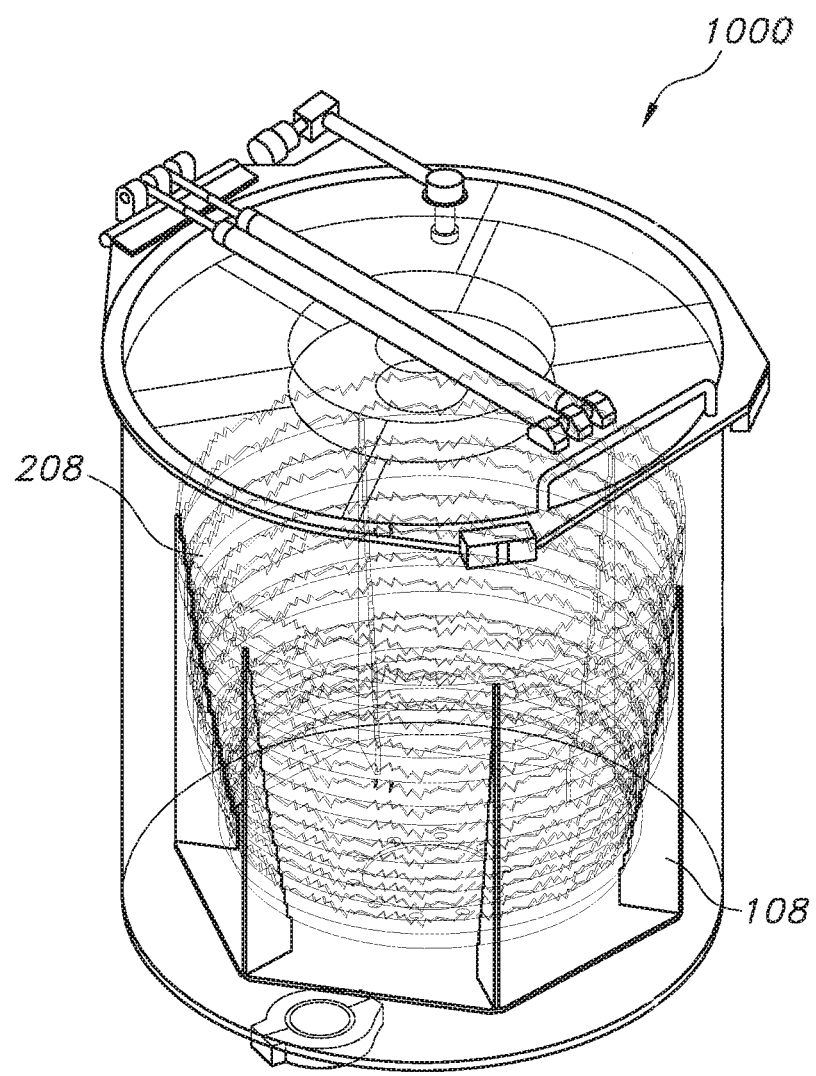
FIG. 23 is a cross-sectional view of the device chamber.
Figure 24:
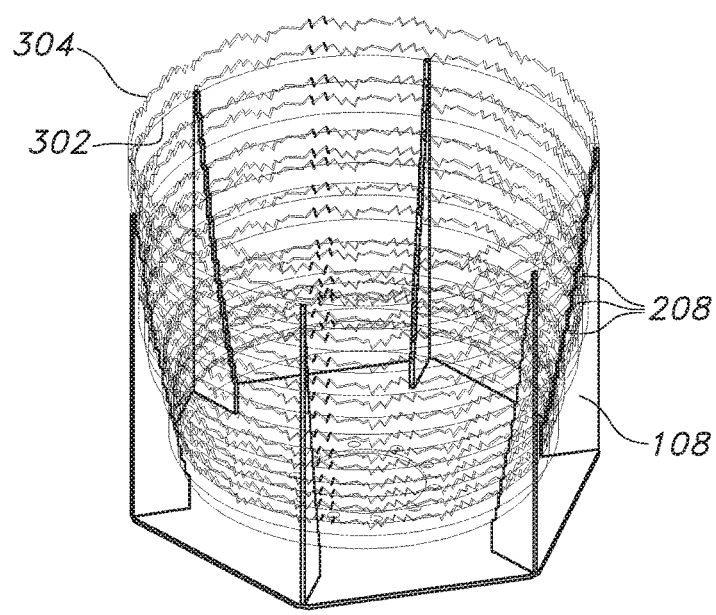
FIG. 24 is a perspective view of the ring rack with the rings.
Figure 25:
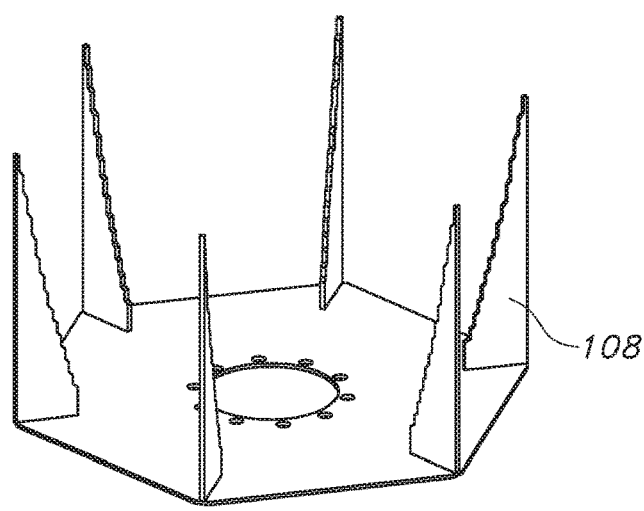
FIG. 25 is a perspective view of the ring rack without the rings.
Figure 26:
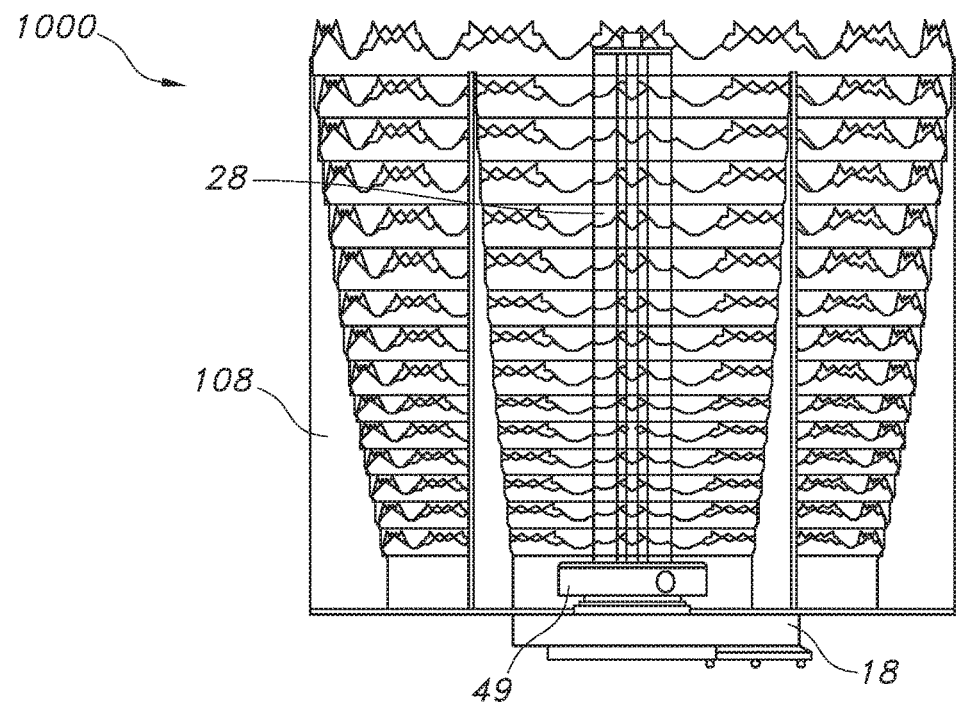
FIG. 26 is a side view of the ring rack and weighing mechanism with the weighing mechanism in a lowered position.
Figure 27:
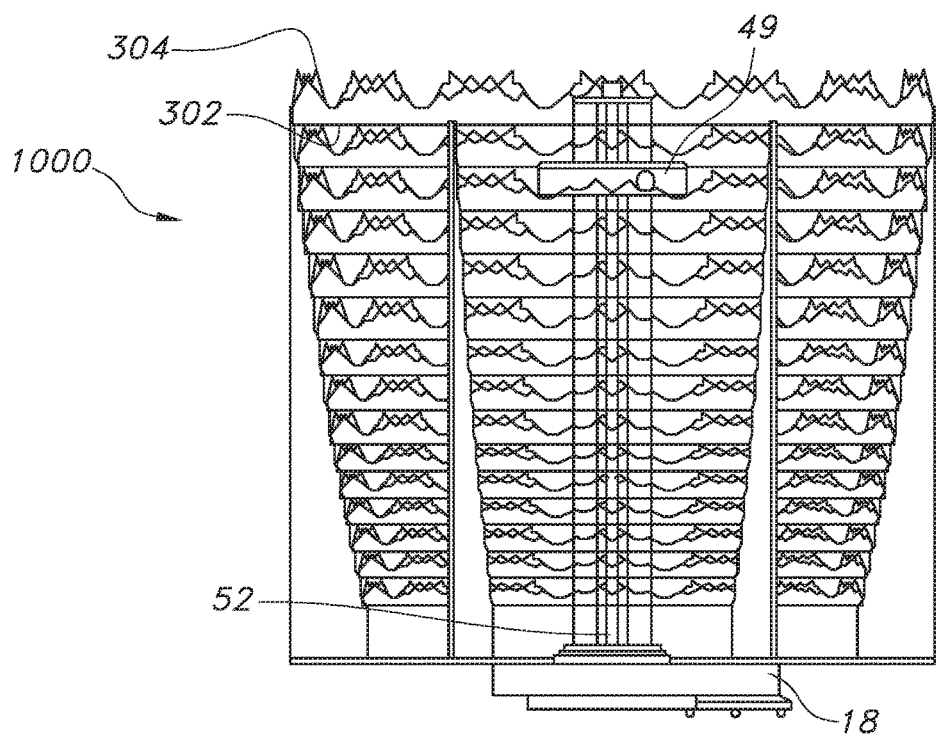
FIG. 27 is a side view of the ring rack and weighing mechanism with the weighing mechanism in a top position.

Referring again to FIGS. 1-4 along with FIG. 22, the computer system 90 includes an electronics module 92, a computer 94, a display unit 96, and an input unit 98, and controls the aggregate mixture analysis device 100. The input unit may be any suitable data entry and control device such as, for example, a keyboard and mouse or a touch screen. In the embodiment shown, the display unit 96 and the computer 94 are each contained within the chassis lid 4. The computer 94 connects to the electronics module 92 and the electronics module 92 is connected to the first stepper motor 26, the second stepper motor 48, the first water pump 84, the second water pump 86 and the vacuum pump. The connections may be made by any suitable cable, for example, CATV cables.

Computer software (not shown) is provided that allows a user to control the aggregate mixture analysis device 100 and calculate and display analysis results.

FIGS. 23-26 illustrate a second embodiment of the sorting unit 1000 where the sieve container is a ring cage 108 that is affixed to the first gear 16. A plurality of rings 208 are affixed to the sides of the ring cage 108. The rings have a smooth bottom edge 302 and a top edge that has a vertical displacement contour 304 that causes vertical oscillation of the ring cage 108 when rotated. The rings 208 and ring cage 108 are generally cylindrical in shape, with the ring cage 108 narrower at the bottom than at the top and with each successive ring 208 having a slightly greater diameter than the ring 208 immediately beneath it. A sieve 44 sits loosely on top of the each of the rings 208, each successively lower sieve 44 having a smaller sieve size, i.e., smaller apertures 45.

As in the first embodiment, actuating the first stepper motor 22 drives the second gear 18 which turns the first gear 16, causing the ring cage 208 to rotate. The sieves 44 are held in position in the horizontal plane by means of the elevator post 306. As the rings 208 rotate, the vertical displacement contour 304 causes the sieves to oscillate in the vertical plane, thereby agitating the sample, which causes it to break into particles. Depending on particle size, the particles drop down through one or more of the sieves 44, with each successive sieve 44 having smaller size apertures 45.

It is understood that the embodiments described herein are merely illustrative of the present invention. Variations in the construction of the portable self-cleaning aggregate mixtures analysis device may be contemplated by one skilled in the art without limiting the intended scope of the invention herein disclosed and as defined by the following claims.

What is claimed is:

1. A aggregate mixture analysis device for sorting a sample mixture of aggregate particles into separate particles and analyzing composition of the sample, the device comprising:
   a material analysis chamber;
   a sorting unit mounted within the material analysis chamber, the sorting unit including a vertical oscillator and a graduated sieve unit having a plurality of sieves for sorting the separate particles according to particle size;
   an elevator post that is centered and mounted on the bottom of the material analysis chamber and that extends vertically upward from the bottom of the material analysis chamber through the graduated sieve unit;
   a moisture evacuation unit for evacuating moisture from the material in the material analysis chamber;
   a weighing unit mounted on the elevator post for weighing the particles captured on each sieve of the plurality of sieves; and
   a washing unit coupled to the material analysis chamber for cleansing the material analysis chamber of particle residue from the sample of aggregate mixture;
   wherein the vertical oscillator includes an oscillation ring that is cylindrical in shape and has a top edge that is a vertical displacement contour, the oscillation ring being attached to a first motor that forces the oscillation ring to rotate, and wherein rotating the oscillation ring forces the graduated sieve unit to oscillate in the vertical plane; and
   wherein the sample mixture of aggregate particles is placed on the uppermost sieve and the vertical oscillator actuated, thereby causing the sample of aggregate mixture to separate into the separate particles that then, depending on a particle size of each particle, drop through the graduated sieve unit until the particles are captured on one of the plurality of sieves that has an aperture size smaller than the particle size.

2. The device of claim 1, wherein the graduated sieve unit includes a plurality of sieve support rings that are circular in shape and correspond in number to the plurality of sieves, and wherein the sieves sit loosely on top of the sieve support rings, and wherein the sorting unit includes a series of stepped ring mounts for holding the sieve support rings.

3. The device of claim 2, further comprising a second motor that is connected to a threaded rod that extends along a central axis in the elevator post and wherein actuating the second motor causes the threaded rod to rotate in a circular direction and raise or lower the weighing unit, depending on the direction of rotation, and wherein, as the weighing unit rises up, the elevator shaft lifts each sieve support ring and calculates the weight of the particles in the sieve, transmitting the weight to a computer system that is integrated into the aggregate mixture analysis device.

4. The device of claim 3, further comprising a washing unit that includes a water tank that is connected to a first water pump and a water filter, the first water pump being connected to a tube that connects to a nozzle located inside the material analysis chamber;
   a drain pipe that connects to the bottom of the material analysis chamber and extends out from the chamber to a second water pump that is connected to the water filter; and
   wherein actuating the first water pump deliver waters from the water tank through the nozzle to spray the inside of the material analysis chamber and wherein actuating the second pump drains water from the bottom of the material analysis chamber through the filter and into the water tank.

5. The device of claim 4 wherein the material analysis chamber, moisture evacuation unit, washing unit and computer system are enclosed in a chassis having a lid and wheels.

6. The device of claim 5, wherein the first motor is affixed to the outside of the material analysis chamber and wherein the first motor is connected to a second gear that connects to a first gear that connects to the oscillation ring, and wherein actuating the motor forces the ring to rotate in a circular direction.

7. A aggregate mixture analysis device for sorting a sample mixture of aggregate particles into separate particles and analyzing composition of the sample, the device comprising:
   a material analysis chamber;
   a sorting unit mounted within the material analysis chamber, the sorting unit including a vertical oscillator and a graduated sieve unit having a plurality of sieves for sorting the separate particles according to particle size;
   an elevator post that is centered and mounted on the bottom of the material analysis chamber and that extends vertically upward from the bottom of the material analysis chamber through the graduated sieve unit;
   a moisture evacuation unit for evacuating moisture from the material in the material analysis chamber;
   a weighing unit mounted on the elevator post for weighing the particles captured on each sieve of the plurality of sieves; and
   a washing unit coupled to the material analysis chamber for cleansing the material analysis chamber of particle residue from the sample of aggregate mixture;
   wherein the sorting unit comprises a ring cage that is placed in the bottom of the material analysis chamber and is connected to a first motor, the ring cage having a plurality of sieve support posts, and a plurality of rings each having a top edge that is a vertical displacement contour and a smooth bottom edge and that are affixed to the sieve support posts;
   wherein the sieves are placed on top of the rings and wherein actuating the first motor causes the ring cage to rotate in a circular motion while the elevator post maintains the sieves in a fixed position in the horizontal plane, thereby causing the sieves to oscillate in the vertical plane; and
   wherein the sample mixture of aggregate particles is placed on the uppermost sieve and the vertical oscillator actuated, thereby causing the sample of aggregate mixture to separate into the separate particles that then, depending on a particle size of each particle, drop through the graduated sieve unit until the particles are captured on one of the plurality of sieves that has an aperture size smaller than the particle size.

\* \* \* \* \*